United States Patent
Viola et al.

(10) Patent No.: US 10,849,619 B2
(45) Date of Patent: Dec. 1, 2020

(54) SHAPE MEMORY FASTENERS AND METHOD OF USE

(71) Applicant: Covidien LP, Mansfield, MA (US)

(72) Inventors: Frank Viola, Sandy Hook, CT (US); Gerald Hodgkinson, Guilford, CT (US)

(73) Assignee: Covidien LP, Mansfield, MA (US)

(*) Notice: Subject to any disclaimer, the term of this patent is extended or adjusted under 35 U.S.C. 154(b) by 1056 days.

(21) Appl. No.: 15/049,503

(22) Filed: Feb. 22, 2016

(65) Prior Publication Data
US 2016/0166252 A1  Jun. 16, 2016

Related U.S. Application Data

(62) Division of application No. 12/895,966, filed on Oct. 1, 2010, now Pat. No. 9,295,463.
(Continued)

(51) Int. Cl.
*A61B 17/064* (2006.01)
*A61B 17/00* (2006.01)
(Continued)

(52) U.S. Cl.
CPC ...... *A61B 17/0644* (2013.01); *A61B 17/0057* (2013.01); *A61B 17/068* (2013.01);
(Continued)

(58) Field of Classification Search
None
See application file for complete search history.

(56) References Cited

U.S. PATENT DOCUMENTS

| 4,485,816 A | 12/1984 | Krumme |
| 4,950,258 A * | 8/1990 | Kawai ............... A61B 17/0644 604/530 |

(Continued)

FOREIGN PATENT DOCUMENTS

| EP | 0460439 A2 | 12/1991 |
| EP | 1552794 A2 | 7/2005 |

(Continued)

OTHER PUBLICATIONS

European Search Report for EP 10251766.1-1269 date of completion is Feb. 14, 2011 (3 pages).

*Primary Examiner* — Shaun L David
(74) *Attorney, Agent, or Firm* — Carter, DeLuca & Farrell LLP (57) ABSTRACT

A surgical fastener configured to close an opening in tissue is provided. The surgical fastener includes a base defining a central axis at least one pair of legs extending from the base. Each of the legs includes a base portion and a tissue engaging portion. When in a first position, each of the tissue engaging portions is arranged to define an insertion direction and when in a second position, each of the tissue engaging portions extends inward towards the central axis. The surgical fastener is at least partially formed from a shape memory material including a combination of Polydioxanone and Poly(L-lactide) or a combination of Trimethylene Carbonate and Poly(L-lactide). The pair of legs are configured to move from the first position to the second position upon activation of the shape memory material.

12 Claims, 8 Drawing Sheets

US 10,849,619 B2
Page 2

Related U.S. Application Data (60) Provisional application No. 61/249,642, filed on Oct. 8, 2009.

(51) Int. Cl.
  *A61B 17/10* (2006.01)
  *A61L 31/04* (2006.01)
  *A61L 31/06* (2006.01)
  *A61B 17/068* (2006.01)
  *A61B 90/00* (2016.01)

(52) U.S. Cl.
  CPC ............ *A61B 17/10* (2013.01); *A61L 31/041* (2013.01); *A61L 31/06* (2013.01); *A61B 2017/00004* (2013.01); *A61B 2017/00867* (2013.01); *A61B 2017/0641* (2013.01); *A61B 2090/037* (2016.02); *A61L 2400/16* (2013.01)

(56) References Cited

U.S. PATENT DOCUMENTS

| | | |
|---|---|---|
| 5,002,563 A | 3/1991 | Pyka et al. |
| 5,120,175 A | 6/1992 | Arbegast et al. |
| 5,246,443 A | 9/1993 | Mai |
| 5,324,307 A | 6/1994 | Jarrett et al. |
| 5,474,557 A | 12/1995 | Mai |
| 5,478,354 A | 12/1995 | Tovey et al. |
| 6,312,447 B1 | 11/2001 | Grimes |
| 6,325,805 B1 | 12/2001 | Ogilvie et al. |
| 6,607,542 B1 | 8/2003 | Wild |
| 6,626,930 B1 | 9/2003 | Allen et al. |
| 6,638,297 B1 | 10/2003 | Huitema |
| 7,112,214 B2 | 9/2006 | Peterson et al. |
| 7,455,682 B2 | 11/2008 | Viola |
| 7,556,647 B2 | 7/2009 | Drews et al. |
| 7,695,471 B2 | 4/2010 | Cheung et al. |
| 7,717,313 B2 | 5/2010 | Criscuolo et al. |
| 9,295,463 B2 | 3/2016 | Viola et al. |
| 2004/0267312 A1 | 12/2004 | Kanner et al. |
| 2005/0021054 A1 | 1/2005 | Ainsworth et al. |
| 2005/0187613 A1* | 8/2005 | Bolduc ............... A61B 17/064 623/1.23 |
| 2008/0017691 A1 | 1/2008 | Hausen |
| 2009/0171363 A1 | 7/2009 | Chocron |
| 2009/0228040 A1 | 9/2009 | Mas et al. |

FOREIGN PATENT DOCUMENTS

| | | |
|---|---|---|
| EP | 1878391 | 1/2008 |
| FR | 2768324 A1 | 3/1999 |
| WO | 2004004578 A1 | 1/2004 |

* cited by examiner

SHAPE MEMORY FASTENERS AND METHOD OF USE

CROSS-REFERENCE TO RELATED APPLICATION

The present application is a divisional of U.S. patent application Ser. No. 12/895,966, filed Oct. 1, 2010, now U.S. Pat. No. 9,295,463, which claims the benefit of and priority from U.S. Provisional Patent Application Ser. No. 61/249,642, filed Oct. 8, 2009, the entire contents of each which are incorporated herein by reference.

BACKGROUND

Technical Field

The present disclosure relates to surgical fasteners. More particularly, the present disclosure relates to a surgical fastener and a method for closing a puncture wound or incision in a patient's tissue.

Background of Related Art

Surgical access devices, including trocars and port assemblies, are known, as are myriad of procedures that may be performed through these devices. Typically, an access device includes a housing and a cannula extending from the housing. The housing may include valves, seals and other mechanisms for directing an instrument into a body cavity of a patient. Cannulas typically are configured to pass through the skin of the patient into the body cavity, i.e., abdomen, either through the use of a bladed tip or through a premade incision.

Upon completion of a procedure, the one or more access devices used to access the body cavity of the patient are removed, thus creating one or more puncture wounds or incisions. The size of the incision may vary depending on the size of the cannula used to access the body cavity. Certain procedures require a larger passageway into the body cavity in which to complete the procedure. Closing the abdominal side of the incision using conventional methods, i.e. staples or sutures, requires either accessing the incision internally or increasing the dimension of the incision to permit manipulation of a suture or stapling device therethrough. As the body cavity is being accessed through the incision being closed, accessing the incision from within the body typically is not an option.

Therefore, it would be beneficial to have a fastener and fastener inserting instrument configured for closing the body cavity side of an opening.

SUMMARY

Accordingly, a surgical fastener configured to close an opening in tissue is provided. The surgical fastener includes a base defining a central axis at least one pair of legs extends from the base. Each of the legs includes a base portion and a tissue engaging portion. When the fastener is in a first position, each of the tissue engaging portions is arranged to define an insertion direction and when in a second position, each of the tissue engaging portions extends inward towards the central axis. The surgical fastener is at least partially formed from a shape memory material including a combination of Polydioxanone and Poly(L-lactide) or a combination of Trimethylene Carbonate and Poly(L-lactide). The pair of legs are configured to move from the first position to the second position upon activation of the shape memory material.

In one embodiment, the shape memory material includes one of 15% Polydioxanone and 85% Poly(L-lactide), 20% Polydioxanone and 80% Poly(L-lactide), 15% Trimethylene Carbonate and 85% Poly(L-lactide) and 20% Trimethylene Carbonate and 80% Poly(L-lactide). It is envisioned that that the shape memory material may include as much as 99% lactide copolymer. The fastener may change from the first position to the second position upon the application of heat. An insertion member may be integrally formed with the base. The tissue engaging portions may include barbs for engaging tissue. The base may include one of an opening or a protrusion configured for operable engagement with an insertion instrument. A frangible connection may be formed between an insertion member and the base. In one embodiment, the fastener includes a second pair of legs.

Also provided is a wound closure apparatus. The apparatus includes an insertion instrument having an elongated shaft and an extension extending from a distal end of the elongated shaft. The extension includes a distal end configured for operable engagement with a surgical fastener. The extension defines one or more vents through which suction may be provided to draw tissue thereabout. The apparatus further includes a fastener having at least one pair of legs movable from a first open position to a second closed position. The fastener is at least partially formed a shape memory material. The legs move from the first position to the second position upon activation of the shape memory material. Each of the legs may include an arcuate shape. Each leg may include a point defining an insertion direction.

Additionally provided is a method of inserting a surgical fastener to close an opening in tissue. The method includes the step of providing an insertion instrument including a surgical fastener releasably secured to the distal end thereof. The surgical fastener has an open configuration and being closable. The method further includes the steps of inserting the distal end of the insertion instrument into the opening, pulling the tissue towards the distal end of the insertion instrument, retracting the insertion instrument proximally through the incision such that legs of the surgical fastener engage tissue, closing the surgical fastener around the tissue, disengaging the insertion instrument from the surgical fastener, and withdrawing the insertion instrument from the incision.

In one embodiment, the method includes applying a vacuum to the tissue. The surgical fastener may be at least partially formed from a shape memory material and the fastener is closed by activation of the shape memory material. The surgical fastener may include a pair of legs. The method may further include the step of rotating the fastener about ninety degrees (90°) after inserting the distal end of the insertion instrument into the opening.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Embodiments of the presently disclosed fastener will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component further away from the user. Although the embodiments of the present disclosure will be described for use in closing an incision through tissue into a body cavity, the presently disclosed fasteners and fastener insertion instruments may be modified for use in closing openings in tissue other than incisions, i.e., lacerations, punctures, or in other areas of the body.

Figure 1:
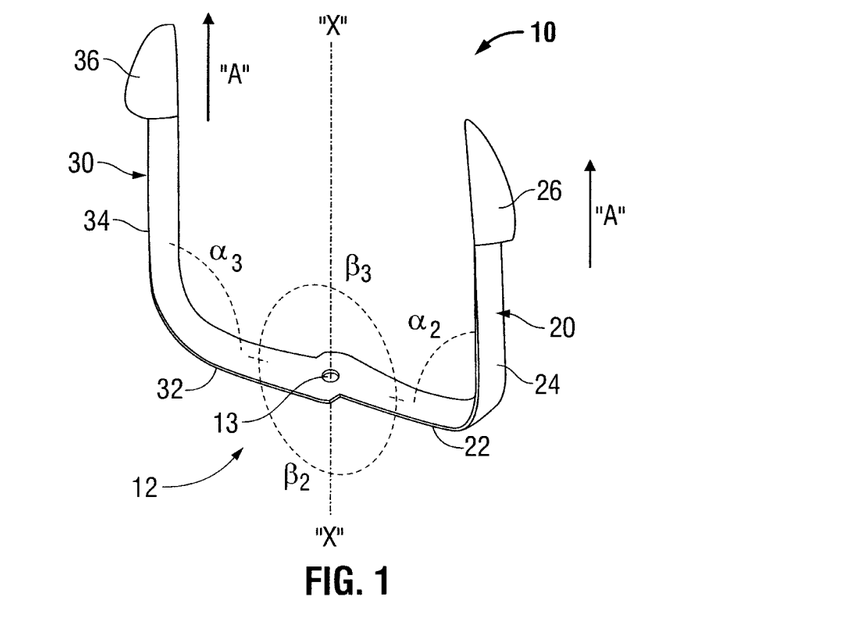
FIG. 1 is a perspective view of an embodiment of a staple according to the present disclosure, in a first or open position.
Figure 2:
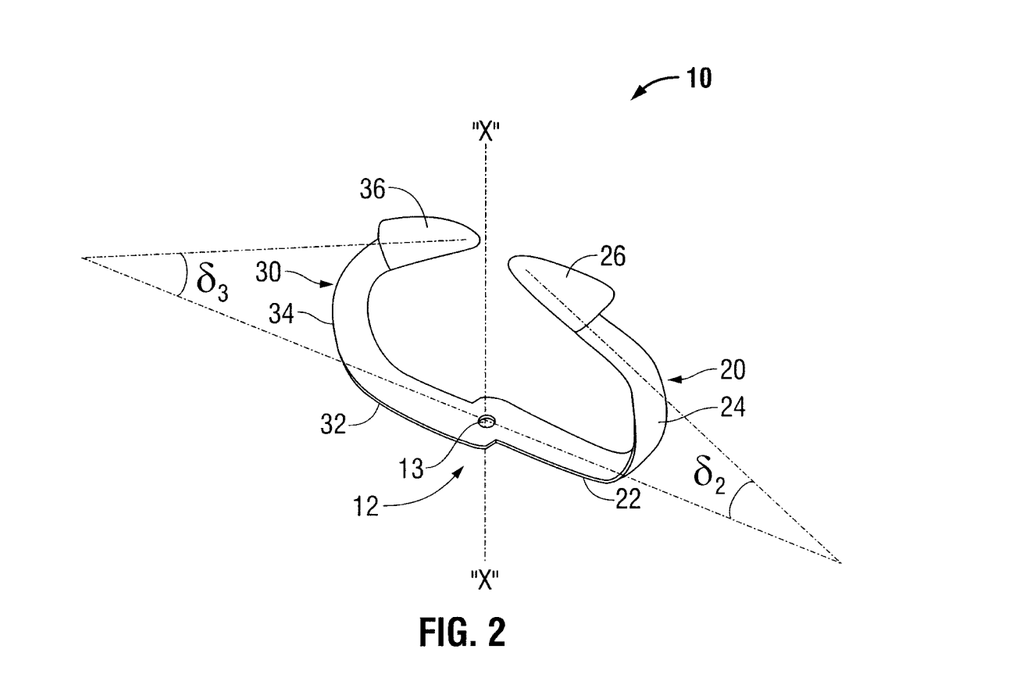
FIG. 2 is a perspective view the staple of FIG. 1, in a second or closed position.

With reference initially to FIGS. 1 and 2, a shape memory fastener according to an embodiment of the present disclosure is shown generally as fastener 10. Fastener 10 is composed of a shape memory material that defines a first configuration at a first temperature, i.e., room temperature, and a second configuration at a second temperature, i.e., body temperature.

Shape memory polymeric materials utilized to form a fastener 10 possess a first phase and a second phase. The first phase (FIG. 1) is a configuration which facilitates insertion of fastener 10 into the tissue of a patient body. The second phase (FIG. 2), which is assumed upon application of heat, such as body heat, is of a configuration which enhances the retention of fastener 10 in the tissue. As will be discussed in further detail below, legs 20 and 30 of fastener 10 possesses an aligned first phase which facilitates insertion into tissue, and a curved second phase configured to engage tissue and close a side of an incision.

Suitable shape memory polymeric materials which may be utilized in a surgical fastener of the present disclosure include, for example, polyurethanes, poly(styrene-butadiene) block copolymers, polynorbornenes, caprolactones, dioxanones, diol esters including oligo (epsilon caprolactone) diol, lactic acid, lactide, glycolic acid, glycolide, ether-ester diols including oligo (p-dioxanone) diol, carbonates including trimethylene carbonate, combinations thereof, and the like. In some embodiments, the shape memory polymer may be a copolymer of two components with different thermal characteristics In other embodiments, blends of bioabsorbable materials may be utilized including, but not limited to, urethanes blended with lactic acid and/or glycolic acid, homopolymers thereof or copolymers thereof, and acrylates blended with caprolactones such as polycaprolactone dimethacrylate poly (butyl acrylate) blends, and combinations thereof.

Several compositions described in U.S. Pat. No. 5,324,307, the contents of which are incorporated by reference herein in its entirety, have been found to demonstrate shape memory effects. Table 1 represents the block copolymers in each system in annealed wire format, the proposed soft and hard segments, and the glass transition temperature ($T_g$), as measured by differential scanning calorimetery, which is equal to $T_{Trans}$. Although the materials listed include a maximum of 85% lactide copolymer, it is envisioned that the material may include as much as 99% lactide copolymer and still exhibit shape memory characteristics.

TABLE 1

SMPs with Proposed Soft and Hard Domains

| Polymer Designation | Composition [mol %] | Soft Domain | Hard Domain | $T_g$ ($T_{Trans}$) [° C.] |
|---|---|---|---|---|
| 15P85L | 15% Polydioxanone 85% Poly(L-lactide) | Polydioxanone and Amorphous Polylactide | Crystalline Polylactide | 54 |
| 20P80L | 20% Polydioxanone 80% Poly(L-lactide) | Polydioxanone and Amorphous Polylactide | Crystalline Polylactide | 45 |
| 15T85L | 15% Trimethylene Carbonate 85% Poly(L-lactide) | Trimethylene Carbonate and Amorphous Polylactide | Crystalline Polylactide | 54 |
| 20T80L | 20% Trimethylene Carbonate 80% Poly(L-lactide) | Trimethylene Carbonate and Amorphous Polylactide | Crystalline Polylactide | 55 |

Preliminary data presented below suggest that the polymer systems in Table 1 undergo a partial shape shift when approaching $T_g$ and that $T_{Trans}$ is depressed when the materials are in aqueous solution. Since it is known that these polymers degrade by water absorption and bulk hydrolysis, it is proposed that water molecules entering the polymer matrices act as plasticizer, causing the soft segments to soften at lower temperatures than in dry air. Polymers exhibiting $T_{Trans}$ depression in aqueous solution would be especially beneficial as implant devices since it should be feasible to maintain the device secondary shape through temperature excursions in the dry state during shipping and storage and still allow shifting at body temperature upon implantation.

Various synthesis and processing methods may be used to tailor $T_{Trans}$ including changes in block segment molar ratios, polymer molecular weight, and time allowed for hard segment formation. $T_{Trans}$ may also be tailored by blending various amounts of low molecular weight oligomers of the soft segment domain material into the parent co-polymer. It is hypothesized that such oligomers would act as plasticizers on the soft domains and cause a downward shift in $T_{Trans}$. $T_{Trans}$ could be easily controlled reproducibly and precisely using a blending method, unlike approaches often described in the literature in which $T_{Trans}$ is controlled by tailoring polymerization reaction parameters. Additionally, the use of trimethylene carbonate (TMC) as a plasticizer may provide the benefit of a self-strengthening device, which becomes stronger and more rigid after being implanted since TMC monomer and low molecular weight TMC oligomers readily diffuse into aqueous environments.

In some embodiments, a molding process is utilized to produce the fastener 10. Plastic molding methods are within the purview of those skilled in the art and include, but are not limited to, melt molding, solution molding and the like. Injection molding, extrusion molding, compression molding and other methods may also be used as the melt molding technique.

Figure 11:
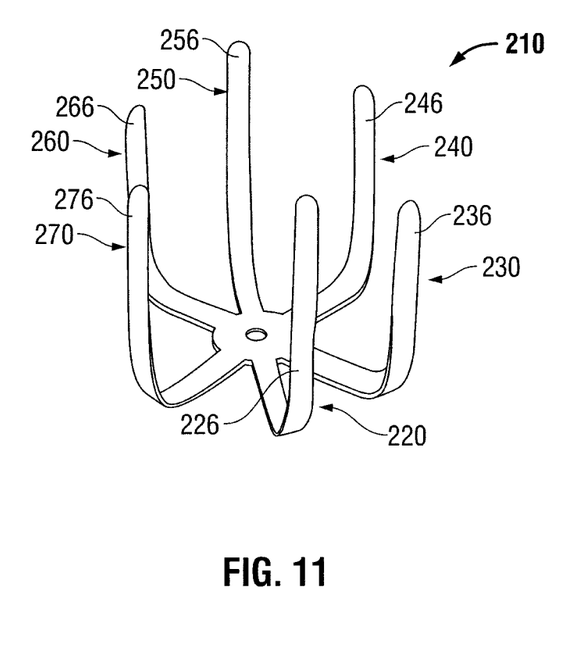
FIG. 11 is a perspective view of another embodiment of a fastener according to the present disclosure, in a first or open position.

With reference still to FIGS. 1 and 2, fastener 10 includes a base 12 and a pair of legs 20 and 30 extending from base 12. Fastener 10 defines a central axis "X" extending therethrough, which also defines an insertion direction "A" (FIG. 1). As will be discussed in further detail below, base 12 includes an opening or detent 13 configured for operable engagement with an insertion instrument. As shown in FIG. 1, fastener 10 includes two (2) legs, however, it is envisioned that fastener 10 may have more or less than two (2) legs, e.g., four legs (FIG. 3) or six legs (FIG. 11). Each of legs 20, 30 includes a base portion 22, 32, a connection portion 24, 34 and a tissue engaging portion 26, 36, respectively. Base portions 22, 32 may be of equal or different lengths and are configured such that fastener 10 may be inserted through an incision or cannula into a body cavity of a patient. Connection portions 24, 34 may be of equal or different lengths and are configured such that when fastener 10 is received in tissue, tissue engaging portions 26, 36 of respective legs 20, 30 do not extend completely through the tissue. In an alternative embodiment, connection portions 24, 34 are configured such that tissue engaging portions 26, 36 extend completely through the tissue in the first or open position. Tissue engaging portions 26, 36 may include an enlarged barbed head, as shown, or may be otherwise suitably configured for piercing and/or engaging tissue. In some embodiments, tissue engaging portions 26, 36 are tapered, curved, angled, and/or pointed at least slightly in the direction of insertion to facilitate insertion of fastener 10 into tissue.

With reference to FIG. 1, in the first phase, fastener 10 includes a first or open position configured for insertion into tissue. In the first or open position, tissue engaging portions 26, 36 of respective legs 20, 30 are maintained substantially parallel to central axis "X". In this manner, connection portion 24, 34, of respective legs 20, 30 define angles $\alpha_2$, $\alpha_3$, respectively, with respect to base portions 22, 32, respectively. In one embodiment, and as shown, angles $\alpha_2$, $\alpha_3$ define an angle of ninety degrees (90°). Angles $\alpha_2$, $\alpha_3$ may each be the same, as shown, or instead, angles $\alpha_2$, $\alpha_3$ may be different. In one embodiment, base portions 22, 32 and connection portions 24, 34 of legs 20, 30, respectively, form curved members.

Figure 16:
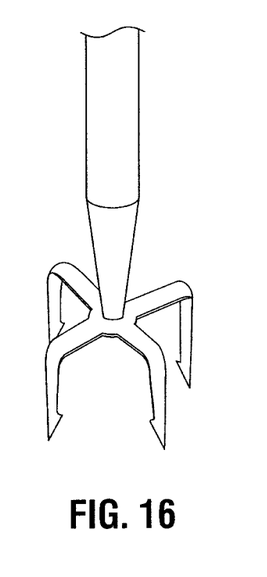
FIG. 16 is a perspective view of an embodiment of a fastener according the present disclosure operably engaged with an alternate embodiment of an insertion instrument.

Turning now to FIG. 2, in the second phase, fastener 10 includes a second or closed position configured for engaging and retaining tissue. In the closed position, tissue engaging portions 26, 36 of respective legs 20, 30 extend radially inward. In one embodiment, tissue engaging portions 26, 36 are maintained substantially perpendicular to the central axis "X". Alternatively, tissue engaging portions 26, 36 may extend radially inward and downwards towards base 12. Each of base portions 22, 32 and connection portions 24, 34 of respective legs 20, 30 maintain a curved configuration defining an angle $\gamma_2$, $\gamma_3$, respectively, therebetween. Angles $\gamma_2$, $\gamma_3$ may be the same, as shown, or instead, angles $\gamma_2$, $\gamma_3$ may be different. In other embodiments, legs 20, 30 are substantially parallel to one another, for example, the fastener could have a substantially "H" shaped-configuration. (FIG. 16)

With reference to FIGS. 1 and 2, in either the first or second phases, base portions 22, 32 of legs 20, 30 define an angle $\beta_2$, $\beta_3$ therebetween. In one embodiment, and as shown, angles $\beta_2$, $\beta_3$ define an angle of one-hundred eighty degrees (180°). Angles $\beta_2$, $\beta_3$ may each be the same, as shown, or instead, angles $\beta_2$, $\beta_3$ may be different.

Figure 3:
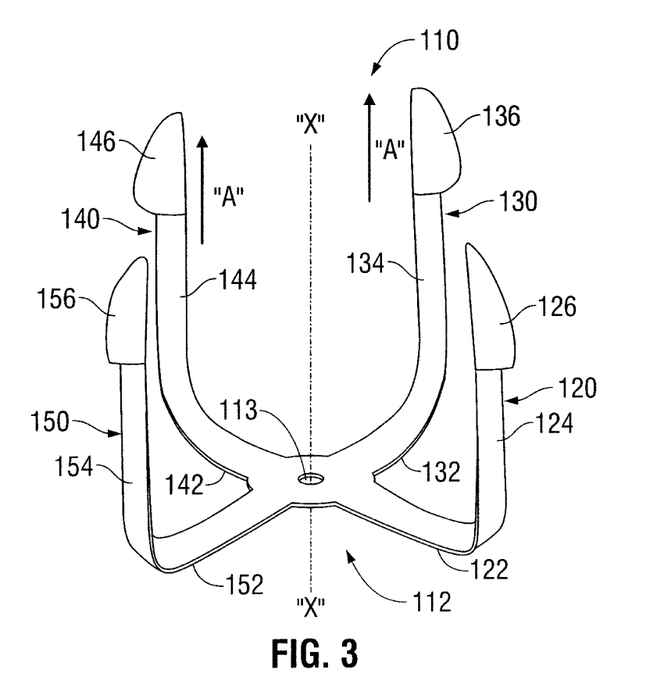
FIG. 3 is a perspective view of an alternate embodiment of a staple according to the present disclosure, in a first or open position.
Figure 4:
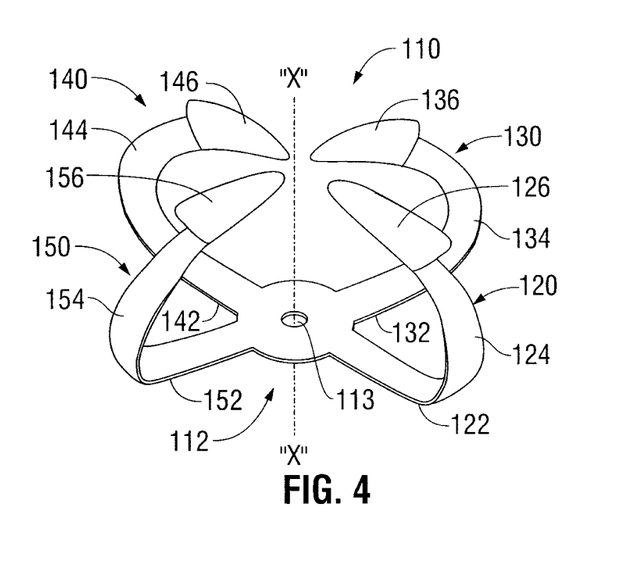
FIG. 4 is a perspective view the staple of FIG. 3, in a second or closed position.

With reference now to FIGS. 3 and 4, fastener 110 is substantially similar to fastener 10 described herein above. Fastener 110 includes a base 112 and two pair of legs 120, 130, 140, 150 extending from base 112. Fastener 110 defines a central axis "X" extending therethrough, which also defines an insertion direction "A". Base 112 includes an opening or detent 113 configured for operable engagement with an insertion instrument. Each of legs 120, 130, 140, 150 includes a base portion 122, 132, 142, 152 a connection portion 124, 134, 144, 154 and a tissue engaging portion 126, 136, 146, 156, respectively. Base portions 122, 132, 142, 152 may be of equal or different lengths and are configured such that fastener 110 may be inserted through an incision or cannula into a body cavity of a patient. Connection portions 124, 134, 144, 154 may be of equal or different lengths and are configured such that when fastener 110 is received in tissue, tissue engaging portions 126, 136, 146, 156 of respective legs 120, 130, 140, 150 do not extend completely through the tissue. In an alternative embodiment, connection portions 124, 134, 144, 154 are configured such that tissue engaging portions 126, 136, 146, 156 extend completely through the tissue in the first or open position.

As discussed above with respect to fastener 10, in the first phase, fastener 110 includes a first or open position (FIG. 3) configured for insertion into tissue. In the first or open position, tissue engaging portions 126, 136, 146, 156 of respective legs 120, 130, 140, 150 are maintained parallel to central axis "X". In the second phase, fastener 110 includes a second or closed position (FIG. 4) configured for engaging and retaining tissue. In the closed position, tissue engaging portions 126, 136, 146, 156 of respective legs 120, 130, 140, 150 extend radially inward. In one embodiment, tissue engaging portions 126, 136, 146, 156 are maintained perpendicular to the central axis "X". Alternatively, tissue engaging portions 126, 136, 146, 156 may extend radially inward and downwards towards base 112.

Figure 5:
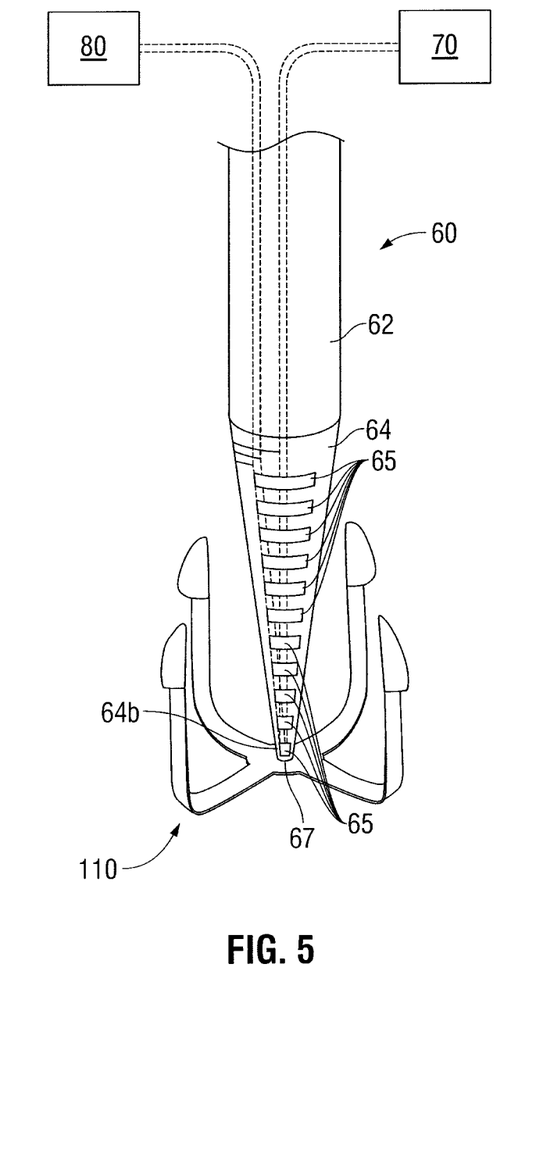
FIG. 5 is a perspective view of the distal portion of an insertion instrument operably connect to a source of heated fluid and a vacuum source and including the fastener of FIGS. 3 and 4 attached thereto.

Turning now to FIG. 5, fastener 110 is shown operably connected to an insertion instrument 60. Insertion instrument 60 includes an elongated shaft 62 having a extension 64 operably extending therefrom. Extension 64 may be tapered, as shown, or may be cylindrical, substantially planar or otherwise configured for insertion through an incision. Extension 64 may be integrally formed, securely connected or releasably connected with elongated shaft 62. Tapered extension 64 includes a distal end 64b configured for operable engagement with fastener 110. As shown, distal end 64b of tapered end 64 is integrally formed with fastener 110 and is configured to break-way from fastener 110 at a predetermined time, i.e., upon deformation of fastener 110 from the open position to the closed position. Alternatively, fastener 110 includes an opening 113 (FIG. 3) through which fastener 110 is selectively engaged by insertion instrument 60. In this manner, fastener 110 is released from insertion instrument 60 through action of the user. It is contemplated that the point of attachment between fastener 110 and distal end 64b may be a frangible connection.

Still referring to FIG. 5, tapered extension 64 includes one or more vents 65. Vents 65 are operably connected to a source of suction 70. As will be discussed in further detail below, suction is provided through vents 65 from suction source 70 to cause opposed sides of incision "I" (FIG. 6) to be drawn about tapered extension 64. Tapered extension 64 may further include an opening 67 formed near distal end 64b operably connected to a source of heated fluid 80. As will also be discussed in further detail below, ejection of a heated fluid (not shown) through opening 67 in tapered extension 64 bathes fastener 110 in the heated fluid, thereby causing fastener 110 to deform from the open position to the closed position. In an alternative embodiment, fastener 110 includes a hollow configuration through which the heated fluid flows to cause the deformation of fastener 110. In yet another embodiment, fastener 110 may include a conductive core capable of heating fastener 110. In this manner, heated fluid source 80 is replaced by a source of electrical energy, and electrical energy is provided to the conductive core to heat fastener 110, thereby causing deformation of fastener 110 from the first position to the second position. Alternatively, fastener 110 may be configured to deform upon application of infrared light, chemical agents, heat or other suitable activating agent.

Figure 6:
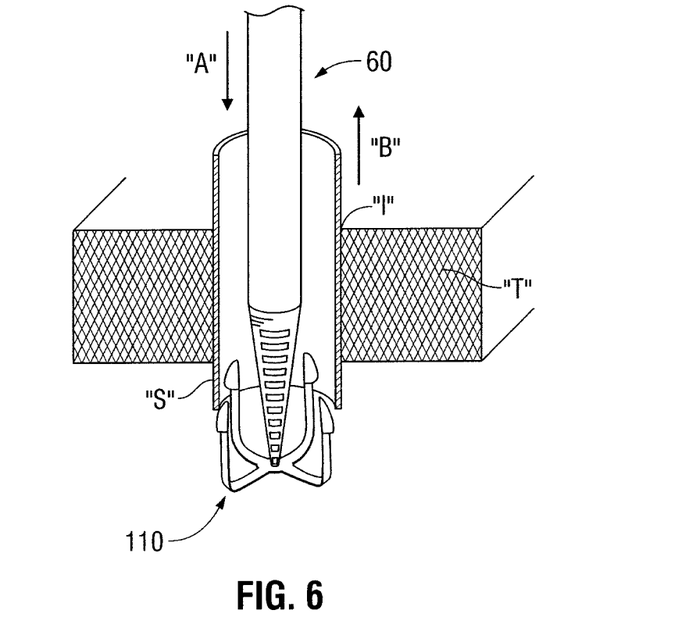
FIG. 6-10 are progressive partial cross-sectional side views of the steps of applying the fastener of FIGS. 3 and 4.
Figure 7:
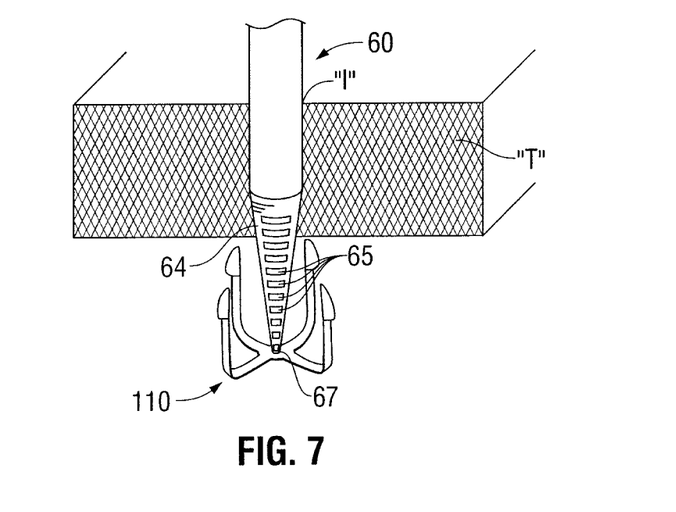

With reference now to FIGS. 6-10, a method of closing an incision "I" using fastener 110 will be described in detail. Although shown with reference to an incision created for receipt of an access assembly, the aspects of the present disclosure may be adapted to close most incisions into a body cavity. Referring initially to FIG. 6, fastener 110 is operably received on distal end 64b of tapered extension 64 of insertion instrument 60. As discussed above, fastener 110 may be integrally formed with tapered extension 64, or otherwise mechanically secured thereto. Although shown being applied using insertion instrument 60, it should be appreciated that other instruments and/or methods may be used to apply fastener 110. Additionally, insertion instrument 60 may be used to apply other fasteners, i.e., fastener 10. Fastener 110 is configured to be received through a cannula or sleeve "S" inserted through an incision "I" in tissue "T" of a patient, as indicated by arrow "A". In an alternate embodiment, fastener 110 and instrument 60 are inserted into a body cavity independently of one another and are subsequently secured together within the body cavity. Once fastener 110 has been inserted through sleeve "S" and received within the body cavity of the patient (FIG. 6), sleeve "S" is removed from tissue "T", as indicated by arrow "B". In this manner, tissue "T" collapses about elongated shaft 62 and tapered extension 64 (FIG. 7). Tissue "T" is further drawn about tapered extension 64 by suction provided from suction source 70 (FIG. 5) through openings 65 formed in tapered extension 64.

Figure 8:
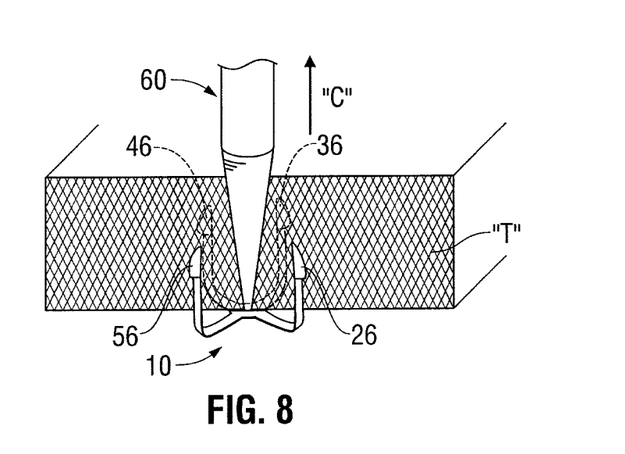

Turning now to FIG. 8, once tissue "T" has been drawn about tapered extension 64 of insertion instrument 60, insertion instrument 60 is pulled proximally through tissue "T", as indicated by arrow "C", thereby causing tissue engaging portions 126, 136, 146, 156 of fastener 110 to be received within tissue "T" about incision "I". Continued retraction of insertion instrument 60 causes further engagement of tissue engaging portions 126, 136, 146, 156 with tissue "T". In one embodiment, once legs 120, 130, 140, 150 of fastener 110 have fully engaged tissue "T", the heat provided by tissue "T" may cause fastener 110 to deform from the open position to the closed position. Alternative, tissue "T" may be temporarily heated above normal body temperature to cause the deformation of fastener 110. In this manner, tissue "T" is heated to $T_g$ (above body temperature) to cause fastener 110 to deform. Since polymers become softer and more flexible above $T_g$, by having $T_g$ above body temperature, once the tissue "T" cools to body temperature, fastener 110 will be stiffer and stronger. In another embodiment, a heated fluid may be provided through opening 67 in extension 64 to bathe fastener 110 in the heated fluid, thereby causing fastener 110 to deform. In yet another embodiment, the heated fluid is directed into and/or through hollow portions (not shown) of fastener 110 to cause the deformation thereof. In still yet another embodiment, a source of electrical energy may be activated to supply a heat inducing core (not shown) within fastener 110 with energy to cause the heating thereof, and thus, deformation of fastener 110.

Figure 9:
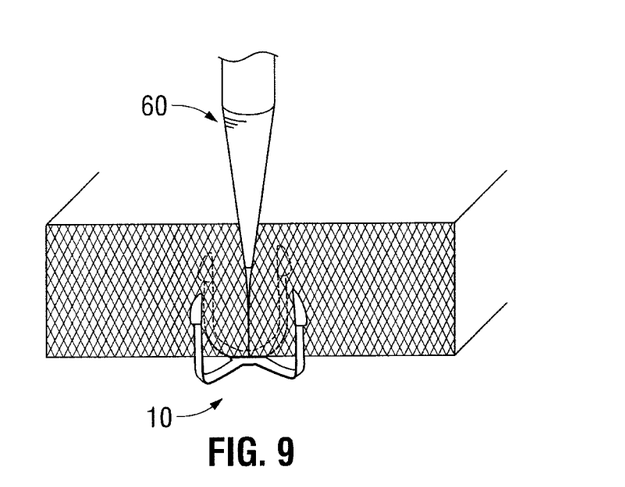

With reference to FIG. 9, prior to or during the deformation of fastener 110 from the open position to the closed position, tapered extension 64 of insertion instrument 60 is separated from fastener 110. As discussed above, tapered extension 64 may be connected to fastener 110 by a breakaway connection that breaks during deformation of fastener 110. Alternatively, insertion instrument 60 includes a release mechanism (not shown) for releasing fastener 110 therefrom. Upon release of fastener 110 from tapered extension 64, insertion instrument 60 is completely removed from incision "I".

Figure 10:
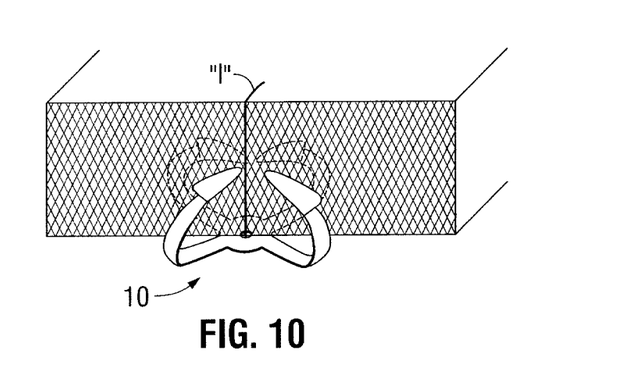

Turning now to FIG. 10, in the closed position, fastener 110 securely engages tissue "T" about an internal or abdominal side of incision "I" thereby closing incision "I". An outer side of incision "I" may be closed in a conventional manner. Alternatively, the insertion instrument can be configured to dispense a wound closure material, such as by including a passage for wound closure material to be carried to a dispersing aperture. The wound closure materials in U.S. Pat. Nos. 7,717,313 and 7,455,682, the entire disclosures of which are hereby incorporated by reference herein, can be used. As discussed above, fastener 110 may instead be configured to extend completely through tissue "T", in which case, external closure of incision "I" may not be necessary. One or more additional fasteners 110 may be applied to tissue "T" in the manner described above.

Figure 12:
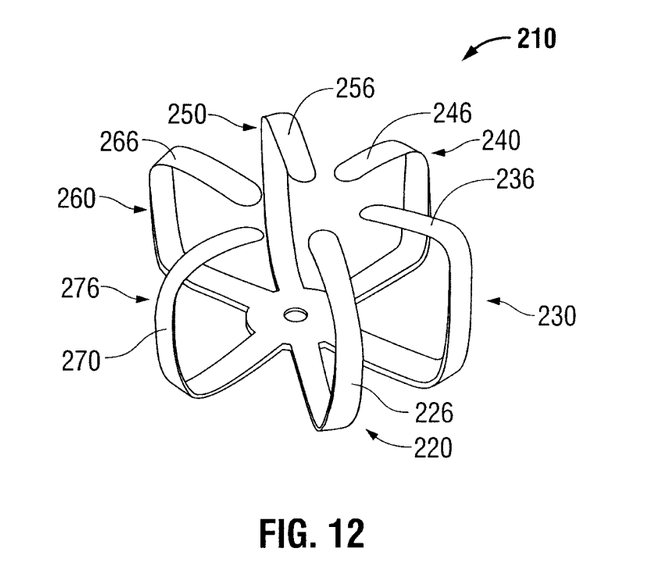
FIG. 12 is a perspective view the fastener of FIG. 11, in a second or closed position.

Turning to FIGS. 11 and 12, an alternate embodiment of a shape memory fastener according to the present disclosure is shown generally as fastener 210. Fastener 210 is substantially similar to fasteners 10, 110 described hereinabove, and therefore, will only be described as relates to the differences therebetween. Fastener 210 includes six legs 220, 230, 240, 250, 260, 270 for more securely closing an incision formed in tissue. Tissue engaging portions 226, 236, 246, 256, 266, 276 of legs 220, 230, 240, 250, 260, 270, respectively, are tapered or pointed to facilitate insertion into tissue.

Figure 13:
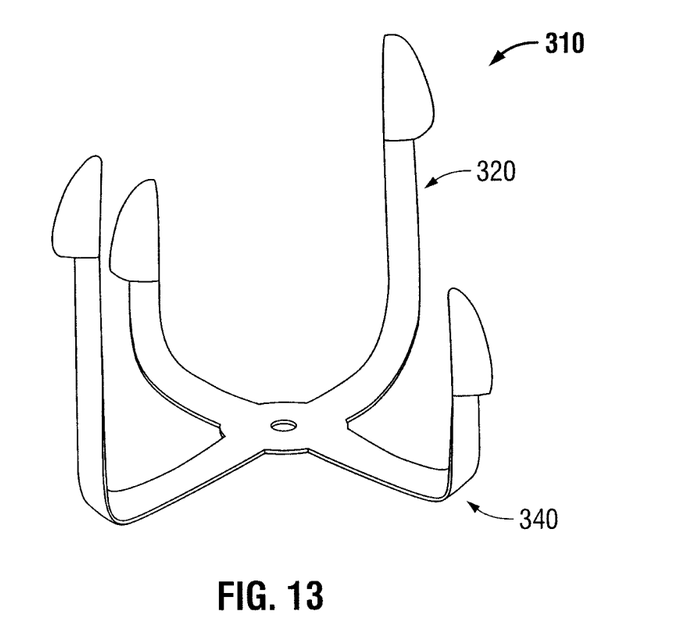
FIG. 13 is a perspective view of still yet another embodiment of a fastener according to the present disclosure, in a first or open position.
Figure 14:
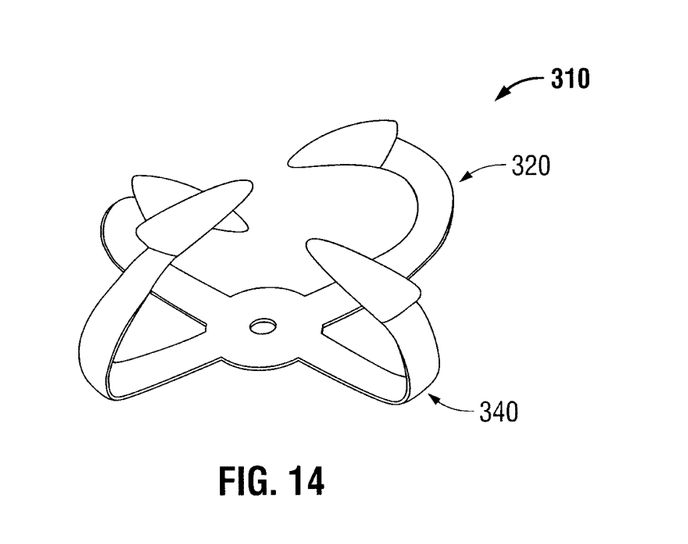
FIG. 14 is a perspective view the fastener of FIG. 13, in a second or closed position.

With reference to FIGS. 13 and 14, yet another embodiment of a shape memory fastener according to the present disclosure is shown generally as fastener 310. Fastener 310 is substantially similar to fasteners 10, 110, 210 described hereinabove. Fastener 310 includes a first pair of legs 320 and a second pair of legs 340. Each of first and second pairs of legs 320, 340 are of a different lengths. As shown, each pair of legs 320, 340 assumes a different configuration in the closed position (FIG. 14). In this manner, fastener 310 is configured to more securely engage tissue.

Figure 15:
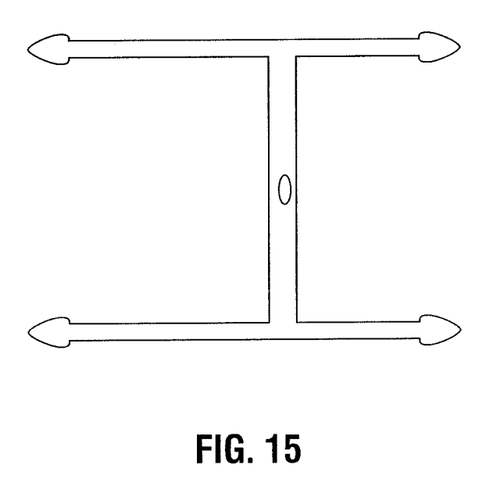
FIG. 15 is a top view of yet another embodiment of a fastener according to the present disclosure.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure. For example, fastener 10 may be formed of a material that causes legs 120, 130 to be in a closed first position and when cooled below a predetermined temperature assumes an open second position. In this manner, fastener 110 is inserted within tissue "T" when in the cooled second position, and upon engagement with heated body "T", fastener 110 returns to the closed first position. In another embodiment, fastener 10 is configured to be pushed into tissue from the outside to close the skin, muscle layer, etc. (FIG. 15)

The invention claimed is:

1. A method of inserting a surgical fastener to close an opening through tissue, the method comprising:
   providing an insertion instrument including a surgical fastener integrally formed with and configured to break-away from a distal end of the insertion instrument, the surgical fastener having an open configuration and being closable;
   inserting the distal end of the insertion instrument into the opening through tissue;
   approximating at least one of tissue or the distal end of the insertion instrument towards the other of the distal end of the insertion instrument or tissue;
   retracting the insertion instrument proximally through the opening such that legs of the surgical fastener engage tissue;
   closing the surgical fastener within tissue;
   disengaging the insertion instrument from the surgical fastener such that the surgical fastener breaks-away from the insertion instrument; and
   withdrawing the insertion instrument from the opening.

2. The method of claim 1, further including applying a vacuum to draw tissue to the distal end of the insertion instrument.

3. The method of claim 1, wherein providing the insertion instrument includes the surgical fastener being at least partially formed from a shape memory material and closing the surgical fastener within tissue includes activating the shape memory material.

4. The method of claim 1, wherein providing the insertion instrument includes the surgical fastener having a pair of legs, and inserting the distal end of the insertion instrument into the opening through tissue further includes rotating the surgical fastener about ninety degrees.

5. The method of claim 1, wherein providing the insertion instrument includes the surgical fastener being secured to the insertion instrument by a frangible connection, and disengaging the insertion instrument from the surgical fastener includes breaking the frangible connection.

6. The method of claim 1, wherein providing the insertion instrument includes the surgical fastener having a conductive core, and closing the surgical fastener around tissue includes heating the conductive core.

7. The method of claim 1, wherein providing the insertion instrument includes at least a portion of the surgical fastener being hollow, and closing the surgical fastener around tissue includes delivering a heated fluid through the surgical fastener.

8. The method of claim 1, wherein providing the insertion instrument includes the insertion instrument having a release mechanism, and disengaging the insertion instrument from the surgical fastener includes activating the release mechanism.

9. The method of claim 1, wherein disengaging the insertion instrument from the surgical fastener includes the surgical fastener breaking-away from the distal end of the insertion instrument upon a deformation of the surgical fastener.

10. A method of inserting a surgical fastener to close an opening through tissue, the method comprising:
    inserting a distal end of an insertion instrument into the opening through tissue, wherein a surgical fastener is integrally formed with and configured to break-away from the distal end of the insertion instrument;
    retracting the insertion instrument proximally through the opening such that legs of the surgical fastener that is secured to the distal end of the insertion instrument engage tissue;
    disengaging the insertion instrument from the surgical fastener such that the surgical fastener breaks-away from the insertion instrument; and
    withdrawing the insertion instrument from the opening.

11. The method of claim 10, further including applying a vacuum to draw tissue to the distal end of the insertion instrument.

12. The method of claim 10, wherein disengaging the insertion instrument from the surgical fastener includes the surgical fastener breaking-away from the distal end of the insertion instrument upon a deformation of the surgical fastener.

* * * * *